United States Patent [19]
Eklund et al.

[11] Patent Number: 5,676,294
[45] Date of Patent: Oct. 14, 1997

[54] RETENTION DEVICE FOR INTRAVENOUS FLUID CONTAINER

[75] Inventors: Roger L. Eklund; Carlton Samuel Phillips, both of League City; Miguel A. Hernandez, Jr., Houston, all of Tex.

[73] Assignee: Medical Invention Research Company, Houston, Tex.

[21] Appl. No.: 637,535

[22] Filed: Apr. 25, 1996

[51] Int. Cl.$^6$ .................................................... A45F 3/14
[52] U.S. Cl. .................... 224/625; 224/623; 224/647; 224/265; 224/148.7; 128/DIG. 6
[58] Field of Search ........................... 224/191, 600, 224/603, 604, 605, 623, 625, 626, 637, 638, 259, 262, 148.1, 148.2, 148.7, 148.4, 901, 901.4, 901.8, 250, 264, 647, 645, 271, 272, 257, 265; 128/DIG. 6, DIG. 15, 877

[56] References Cited

U.S. PATENT DOCUMENTS

| | | |
|---|---|---|
| 1,981,076 | 11/1934 | Sells ............................................. 224/264 |
| 2,506,685 | 5/1950 | Sadloski et al. . |
| 2,723,665 | 11/1955 | Goldsmith . |
| 3,282,482 | 11/1966 | Scharsu ......................................... 224/605 |
| 3,482,748 | 12/1969 | Roberts, Jr. .................................. 224/626 |
| 3,547,322 | 12/1970 | Dawson et al. . |
| 4,096,977 | 6/1978 | Barville et al. .............................. 224/605 |
| 4,121,822 | 10/1978 | DiSabatino et al. ......................... 224/603 |
| 4,308,982 | 1/1982 | Hall .............................................. 224/917 |
| 4,438,763 | 3/1984 | Zablen . |
| 4,582,508 | 4/1986 | Palvlka . |
| 4,819,845 | 4/1989 | Bryd ............................................. 224/626 |
| 4,905,882 | 3/1990 | Ross . |
| 5,335,835 | 8/1994 | Hogan .......................................... 224/917 |

Primary Examiner—Henry J. Recla
Assistant Examiner—Gregory M. Vidovich
Attorney, Agent, or Firm—Robert C. Curfiss; Carol M. Nielsen

[57] ABSTRACT

A retention device is provided for supporting the container of intravenous fluids on a patient who is not bedridden. The retention device has a shoulder harness, a top bracket connected to the harness by a pin and a strap engaging and connected to the shoulder harness. The retention device is designed for wide latitude of patient mobility and comfort.

10 Claims, 2 Drawing Sheets

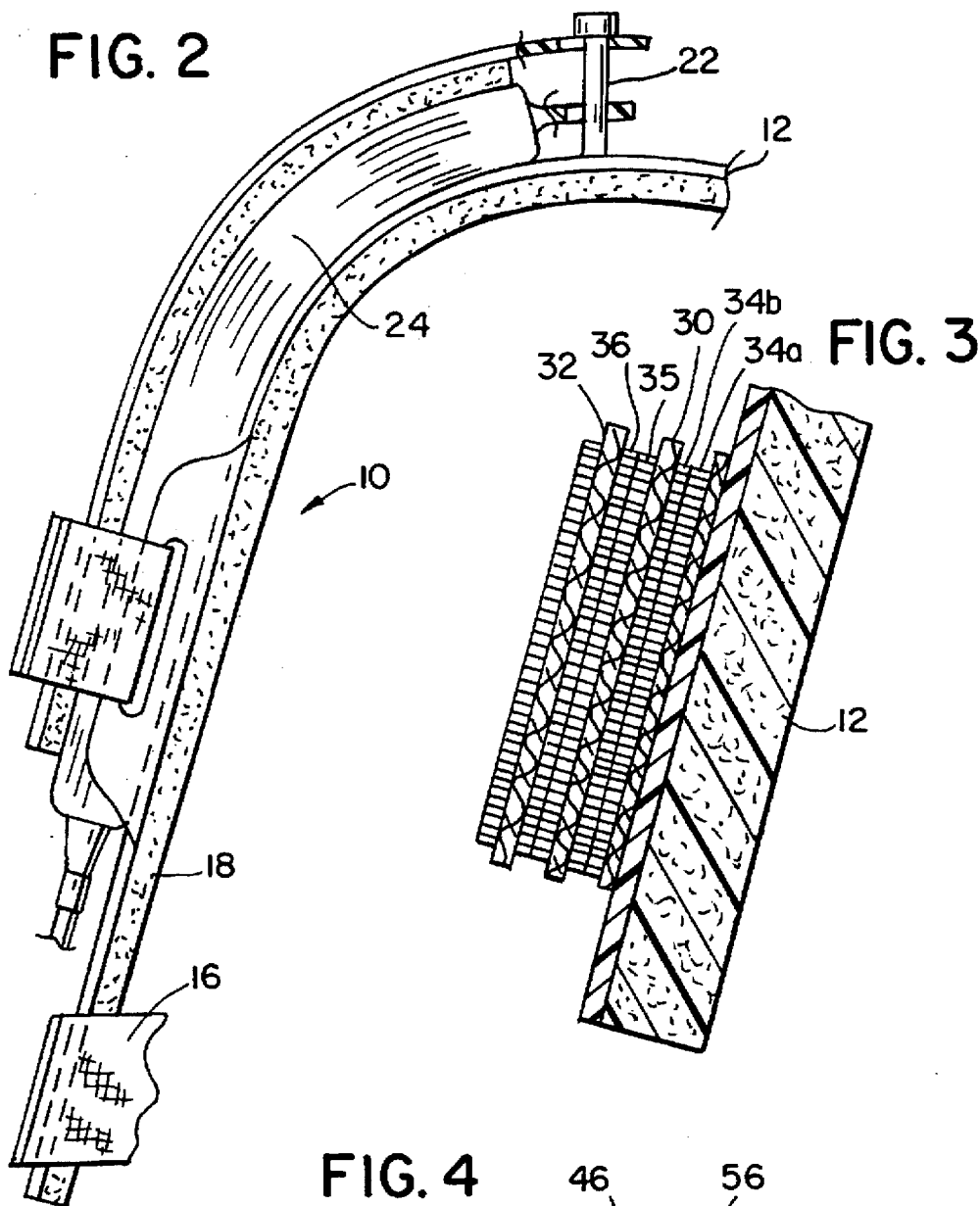

RETENTION DEVICE FOR INTRAVENOUS FLUID CONTAINER

BACKGROUND OF THE INVENTION

1. Field of Invention

This invention is generally related to medical devices for administrating intravenous fluids, and is specifically directed to a carrying device for retaining an intravenous fluid container.

2. Description of Prior Art

Administrating medication to patients intravenously is a well known medical technique. Typically, intravenous feeding is provided to persons who are bedridden. Consequently, the conventional facility adapted to dispense such fluids is a fixed, stationary stand located near the patient. The stand is used to support a bag or other type of fluid container, and makes patient mobility difficult. Certain patients need to receive a substantial amount of medication intravenously. However, the patient may not be incapacitated and require confinement to a bed. Nonetheless, a substantial amount of time is required when medicine must be fed to a patient dropwise through intravenous feeding. Patients are then forced to either stay stationary, or move about with a bulky, hard to maneuver device.

Although there has been attempts to mobilize the patient, prior art devices have fallen short of providing true latitude of movement. Some intravenous fluid container carrying devices require that another person such as a nurse or visitor hand carry the medicine container. Other more portable stations have a mounting container support structure on a movable wheeled cart or affixed to the patient's wheel chair, cart, stretcher or bed.

Certain devices have been developed for the intravenous fluid container to be worn on a person. These prior art devices are bulky, uncomfortable and not very conducive to free flow of patient movement. For example, one such medical apparatus is disclosed in U.S. Pat. No. 3,547,322 issued to Dawson. Adapted to support and carry a container of fluid on a patient, this apparatus is extremely bulky, awkward and uncomfortable for the patient to use. Similarly, U.S. Pat. No. 4,438,763 issued to Zablen provides an ambulatory support means to be used in connection with an intravenous delivery system. The support means consists of a rigid support sized to fit adjacent to the users back. Here, an upwardly extending member is used to carry the intravenous liquid container. Wearing this device, it is next to impossible for the patient to sit down.

Another type of medical device is disclosed in U.S. Pat. No. 4,582,508 issued to Pavelka. This device is designed for holding indwelling catheters under garments. Appearing to offer more comfort to the user, the device is not suitable for an intravenous fluid container for it lacks the effect of gravity on the free flow of fluid necessary to operate the intravenous system. No prior art device has been developed to comfortably accommodate and support the intravenous fluid bag onto the patient.

Other personalized carrying apparatus have also been developed for different types of use. The invention of U.S. Pat. No. 2,506,685 issued to Sadloski is a flashlight holder adapted to be worn on the shoulder of the user leaving his hands free to manipulate tools. Although simple to attach to the body, the shoulder supported flashlight holder cannot be worn underneath clothing and is not adequately designed to restrain a bag of fluid when worn on a person.

A need exists, therefore, for a retention device for an intravenous fluid container which is comfortable to wear on top of, or underneath clothing, and allows the patient to be freely mobile.

SUMMARY OF THE INVENTION

The present invention is a portable retention device for a bag containing intravenous fluids. The subject invention is illustrated in a single preferred embodiment. This portable retention device is particularly suitable for supporting and carrying a bag of intravenous fluid (IV bag). The retention device comprises a shoulder harness, a top bracket and a strap. The shoulder harness has a front end and a back end opposite the front end. The top bracket is connected to the shoulder harness with a pin. The strap engages the back end of the shoulder harness and has two ends. One end of the strap removably attaches to the front end of the shoulder harness. To secure the device to the patient, the straps ends are removably attached to each other. In the preferred embodiment, an IV bag is positioned between the shoulder harness and the top bracket and affixed to the retention device at the pin.

The portable retention device of the subject invention is designed to be comfortable for the patient to wear. The present invention may be worn over or under clothing. This carrying device provides a full range of movement for the wearer. The intravenous feeding system is unaffected because of the bag's position on the body of the wearer allowing a natural, dynamic free flow of fluids from the pull of gravity.

As an option, the intravenous container may be secured and tightened between the shoulder harness and the top bracket with a clamping mechanism. Although not necessary for the retention device to function, the clamping mechanism attaches to the shoulder harness and extends over the top bracket to add pressure to the container, forcing the fluid out and replacing gravity flow. The clamping mechanism may be helpful if the patient wearer wishes to lie down and continue to wear the retention device.

Preferably, the clamping device has two extensions and two clamp straps, each clamp strap being connected to one extension. Each extension is attached to the shoulder harness and extends outwardly therefrom. The clamp straps extend over the top bracket and are designed to be connected to and removed from each other.

The present invention overcomes the awkward construction and overall burdensome nature of the prior art devices. The retention device of the subject invention enables a patient to receive medication through an intravenous delivery system and, at the same time, walk without restriction. This device fits to the patient like a clothing garment as opposed to wearing something that looks and feels like a bird cage. The retention device safely protects the container of intravenous fluid and allows the intravenous system to operate as if it were held up by the conventional stand.

It is, therefore, an object and feature of the subject invention to provide a device for the administration of intravenous fluids to persons who are not bedridden.

It is another object and feature of the invention to provide a device which can be conveniently carried by a patient and which supports an intravenous fluid feeding system.

It is, yet, another object and feature of the invention to provide a retention device which is adapted to support a container of fluid in a position suitable for administering the contents by intravenous means to a patient as the patient moves freely about.

It is still another object and feature of the present invention to provide a device for the administration of intravenous fluids that is comfortable to wear on one's person.

Other objects and features of the subject invention will be readily apparent from the accompanying drawings and description of the preferred embodiment.

DETAILED DESCRIPTION OF THE DRAWINGS

FIG. 2 is a side view of the retention device for an intravenous fluid container showing the optional clamping mechanism.

FIG. 3 is a cross sectional view of the shoulder harness with strap ends attached to each other, as one strap end is attached to the shoulder harness.

FIG. 4 is a cross sectional view of the clamping means with clamps extending over the top bracket and attached to each other.

DETAILED DESCRIPTION OF THE PREFERRED EMBODIMENT

Figure 1:
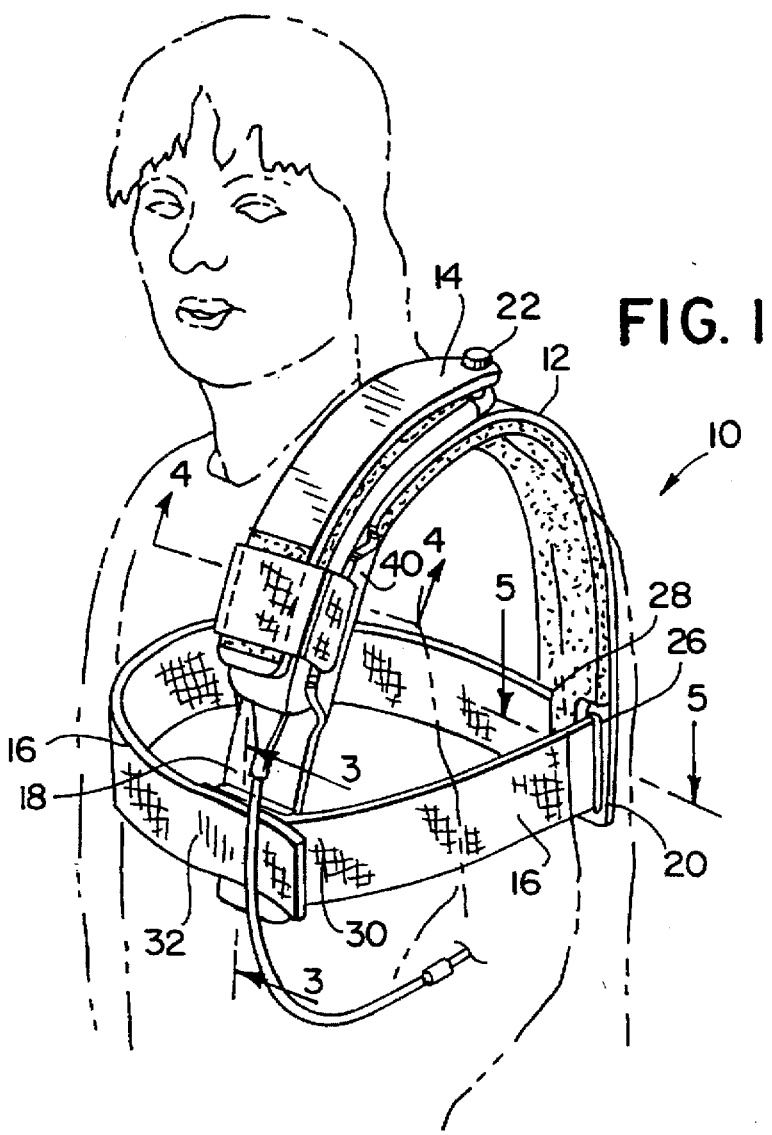
FIG. 1 is a perspective view of the retention device for an intravenous fluid container as worn by the patient.
Figure 5:
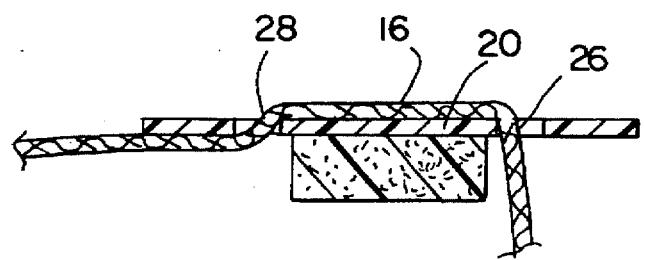
FIG. 5 is a cross sectional view of the strap engaging the shoulder harness at the back end of the shoulder harness.

The preferred embodiment of the retention device for an intravenous fluid container made in accordance with the subject invention is illustrated in FIGS. 1-5 and is designated generally by the reference numeral 10. The retention device for an intravenous fluid container 10 comprises a shoulder harness 12, a top bracket 14, and a strap 16.

The shoulder harness 12 has a front end 18 and a back end 20 and may be worn over either shoulder of the patient. The front end 18 of the shoulder harness 12 downwardly extends from the patient's shoulder and over the patient's chest. The back end 20 of the shoulder harness 12 downwardly extend of the same shoulder and over the patient's back. The shoulder harness 12 may be made of a single or multiple layers of plastic, metallic or non metallic material and may also have a padded layer for extra comfort.

The top bracket 14 connects to the shoulder harness 12 by a pin 22. Like the shoulder harness 12, the top bracket 14 may be made of a plastic or other polymer substance, or metallic material and may also have a padded layer. As shown in FIG. 2, the container of intravenous fluid 24, typically a bag or other similar flexible object, is placed between the shoulder harness 12 and the top bracket 14. The container 24 is attached to the pin 22. The top bracket 14 shields the container of intravenous fluids 24 and acts as cover. The pin 22 may also be made from various materials both metallic and non-metallic.

In the preferred embodiment and as shown with particularity in FIG. 2, the pin 22 is extended through an opening (not shown) in the intravenous fluid container 24 and screws into the shoulder harness 12. The pin 22, however, may be press fitted or be affixed to the shoulder harness 12 by other equivalent means well known to those skilled in the art. Furthermore, the intravenous fluid container 24 may hook onto the pin 22 after the pin 22 is affixed to the shoulder harness 12. The strap 16 engages the shoulder harness 12 at the back end 20 of the shoulder harness 12. As shown in detail in FIG. 5, in the preferred embodiment, the strap 16 slidably engages the back end 20 of the shoulder harness 12 by looping into and out of two openings 26, 28 that are positioned in the back end 20. The strap 16 has two ends 30, 32. The ends 30, 32 are designed to be wrapped around the patient and attached to each other 30, 32 at the front end 18 of the shoulder harness 12. As shown in FIG. 3, only one end 30 attaches to the shoulder harness 12.

Preferably, the strap ends 30, 32 are attached to each other and to the shoulder harness 12 with a first set of VELCRO or hook and loop type fasteners 34a, 34b, 35, 36. The VELCRO fasteners 34b, 35 are attached to both sides of the one end 30 of the strap 16 to allow for attachment to the shoulder harness 12. The VELCRO fastener 36 is attached to the other end 32 of the strap 16. The opposite end 32 of the strap 16 has only one VELCRO type fastener 36 attached to it. Other type of fastening mechanisms may be utilized to attach the strap ends 30, 32 to the front end 18 of the shoulder harness 12 and to each other.

As shown in FIG. 1 and FIG. 4, the retention device may comprise an option clamping mechanism 38 attached to the shoulder harness 12 which extends over the container 24 and top bracket 14. The clamping mechanism 38 may be as simple as a single clamp strap (not shown) that ties around the shoulder harness 12, container of intravenous fluid 24 and top bracket 14. The clamping mechanism 38 may be useful when the patient anticipates bending over a lot or when the patient wishes to lie down. However, the clamping mechanism 38 is not required for the retention device to be functional.

As shown in the figures, the preferred clamping mechanism 38 comprises two extensions 40, 42 and two clamp straps 44, 46. Each extension 40, 42 is attached to the shoulder harness 12 and extends outwardly therefrom. Each extension 40, 42 has an opening 48, 50. Each clamp strap 44, 46 connects to one extension 40, 42 through its opening 48, 50. Each clamp strap 44, 46 extends over the top bracket 14 is secured to the other clamp strap 44, 46 through the use of a second set of VELCRO fasteners 52a, 52b, 54, 56, or the equivalent. As shown in FIG. 4, only one clamp strap 44 is additionally secured to the top bracket 14 with a VELCRO fastener 56, or equivalent means.

To utilize the retention device 10 of the subject invention, the shoulder harness 12 is placed over the shoulder of the patient. The top bracket 14 and intravenous fluid container 24 are then placed over the shoulder harness 12 and connected by the pin 22. Alternatively, the top bracket 14 is first connect to the shoulder harness 12 and placed over the shoulder of the patient. The intravenous fluid container 24 is then hooked onto the pin 22. The strap 16 is fitted around the patient and secured to the front end 18 of the shoulder harness 12. If preferred, the clamping mechanism 38 is then fastened over the intravenous fluid container 24 and top bracket 14.

The foregoing detailed description has been given only by way of example and various modifications will be readily apparent to those skilled in the art.

What is claimed is:

1. A retention device for an intravenous fluid container comprising:

a. a shoulder harness having a front end and a back end opposite said front end, b. a top bracket in spaced relationship to said shoulder harness wherein the intravenous fluid container adapted to be held and is positioned between said shoulder harness and said top bracket, said top bracket connected to said shoulder harness with a pin; and c. a strap engaging said shoulder harness at said back end, said strap having two ends, one said end of said strap removably attached to said front end of said shoulder harness, said ends of said strap being removably attached to each other.

2. The portable retention device of claim 1 further comprising a clamping mechanism, said clamping mechanism attached to said shoulder harness and extending over said top bracket.

3. The portable retention device of claim 1 wherein said strap extends through said shoulder harness at said back end.

4. The portable retention device of claim 2 wherein said clamping mechanism comprises two extensions, each said extension being attached to said shoulder harness and extending outwardly therefrom.

5. A retention device for an intravenous fluid container comprising:

a. a shoulder harness having a front end and a back end opposite said front end;

b. a top bracket in spaced relationship to said shoulder harness, said top bracket connected to said shoulder harness with a pin;

c. a strap engaging said shoulder harness at said back end, said strap having two ends, one said end of said strap removably attached to said front end of said shoulder harness, said ends of said strap being removably attached to each other, said strap extends through said shoulder harness at said back end; and d. a clamping mechanism, said clamping mechanism attached to said shoulder harness and extending over said top bracket, said clamping mechanism comprises two extensions, each said extension being attached to said shoulder harness and extending outwardly therefrom, said clamping mechanism further comprises two clamp straps, each said clamp strap connected to one said extension, said clamp straps extending over said top bracket and removably attached to each other.

6. A retention device for an intravenous fluid container comprising:

a. a shoulder harness having a front end and a back end opposite said front end;

b. a top bracket in spaced relationship to said shoulder harness, said top bracket connected to said shoulder harness with a pin;

c. a strap engaging Said Shoulder harness at said back end, said strap having two ends, one said end of said strap removably attached to said front end of said shoulder harness, said ends of said strap being removably attached to each other, said strap extends through said shoulder harness at said back end; and b. a clamping mechanism, said clamping mechanism attached to said shoulder harness and extending over said top bracket, said clamping mechanism comprises two extensions and two clamps, each said extension being attached to said shoulder harness and extending outwardly therefrom, each said clamp strap connected to one said extension, said clamp straps extending over said top bracket and removably attached to each other, said clamp straps are attached to each other with a hook and loop fastener.

7. A retention device for an intravenous fluid container comprising:

a. a shoulder harness having a from end and a back end opposite said front end opposite said from end, said shoulder harness having two openings for receiving a strap, said strap slidably engaging said shoulder harness at said back end through said openings, said strap having two ends, one said end of said strap attached to said front end of said shoulder harness, said ends attaching to each other;

b. a top bracket in spaced relationship to said shoulder harness, the intravenous fluid container adapted to be held and positioned between said shoulder harness and said top bracket, said top bracket connected to said shoulder harness with a pin; and c. a clamping mechanism attached to said shoulder harness and extending over said top bracket.

8. The retention device of claim 7 wherein said clamping mechanism comprises a clamp strap.

9. The retention device of claim 7 wherein said clamping mechanism comprises a hook and loop fastener.

10. A retention device for an intravenous fluid container comprising:

a. a shoulder harness for supporting the intravenous fluid container, said shoulder harness having a front end and a back end opposite said from end;

b. a top bracket in spaced relationship to said shoulder harness, said top bracket connected to said shoulder harness with a pin wherein the fluid container is adapted to be positioned between said shoulder harness and said top bracket and the fluid container is adapted to be mounted to said retention device by said pin; and c. a strap engaging said shoulder harness at said back end, said strap having two ends, one said end removably attached to said front end of said shoulder harness, said ends being removably attached to each other.

* * * * *

UNITED STATES PATENT AND TRADEMARK OFFICE
CERTIFICATE OF CORRECTION

PATENT NO. : 5,676,294
DATED : October 14, 1997
INVENTOR(S) : Eklund, et al

It is certified that error appears in the above-identified patent and that said Letters Patent is hereby corrected as shown below:

In Claim 1, column 4, line 50 of the Patent, change "end," to --end;--.

In Claim 5, column 5, line 24 of the Patent, change "damp" to --clamp--.

In Claim 6, column 5, line 35 of the Patent, change "Said Shoulder" to --said shoulder--.

In Claim 6, column 5, line 42 of the Patent, change "b." to --d--.

In Claim 7, column 6, line 9 of the Patent, change "from" to --front--.

In Claim 7, column 6, line 10 of the Patent, change "from" to --front--.

In Claim 10, column 6, line 32 of the Patent, change "from" to --front--.

Signed and Sealed this

Sixth Day of January, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,676,294
DATED : October 14, 1997
INVENTOR(S) : Eklund, et. al.

It is certified that error appears in the above-identified patent and that said Letters Patent is hereby corrected as shown below:

Claim 7, column 6, line 10, change "opposite said front end opposite said from end," to --opposite said front end--.

Signed and Sealed this

Seventh Day of April, 1998

Attest:

Attesting Officer

BRUCE LEHMAN

Commissioner of Patents and Trademarks